US008736452B1

(12) United States Patent
Varahramyan et al.

(10) Patent No.: US 8,736,452 B1
(45) Date of Patent: May 27, 2014

(54) TRANSMISSION DELAY BASED RFID TAG

(75) Inventors: Khodadad Varahramyan, Ruston, LA (US); Mangilal Agarwal, Ruston, LA (US); Sudhir Shrestha, Ruston, LA (US); Jeevan Kumar Vemagiri, Bothell, WA (US); Aravind Chamarti, Painted Post, NY (US); Sireesha Ramisetti, Sunnyvale, CA (US); Mercyma Dee Balachandran, Ruston, LA (US)

(73) Assignee: Louisiana Tech University Research Foundation; a division of Louisiana Tech University Foundation, Inc., Ruston, LA (US)

( * ) Notice: Subject to any disclaimer, the term of this patent is extended or adjusted under 35 U.S.C. 154(b) by 1648 days.

(21) Appl. No.: 12/048,019

(22) Filed: Mar. 13, 2008

Related U.S. Application Data

(63) Continuation-in-part of application No. 11/864,159, filed on Sep. 28, 2007, now Pat. No. 8,179,231.

(60) Provisional application No. 60/827,249, filed on Sep. 28, 2006.

(51) Int. Cl.
*G08B 13/14* (2006.01)
(52) U.S. Cl.
USPC ............... 340/572.7; 340/539.26; 340/539.27
(58) Field of Classification Search
USPC ............... 343/745, 905, 906; 340/540, 568.1, 340/572.1, 572.5, 572.7, 500, 531, 539.1, 340/539.26, 539.27, 10.1
See application file for complete search history.

(56) References Cited

U.S. PATENT DOCUMENTS

| | | | |
|---|---|---|---|
| 4,012,741 A | 3/1977 | Johnson | |
| 4,410,632 A | 10/1983 | Dilley et al. | |
| 5,609,096 A | 3/1997 | Kwon et al. | |
| 6,400,322 B2 | 6/2002 | Fang et al. | |
| 6,812,824 B1 | 11/2004 | Goldinger et al. | |
| 6,906,682 B2 | 6/2005 | Alexopoulos | |
| 7,015,868 B2 | 3/2006 | Puente Baliarde et al. | |
| 7,570,169 B2 * | 8/2009 | Li et al. ...................... | 340/572.7 |
| 2001/0035042 A1 * | 11/2001 | Moseley ........................ | 73/23.2 |

(Continued)

OTHER PUBLICATIONS

Ramisetti, Sireesha, Design and Development of an ID generation circuit for low-cost passive RFID-based applications, 2005.

(Continued)

*Primary Examiner* — Brian Zimmerman
*Assistant Examiner* — An T Nguyen
(74) *Attorney, Agent, or Firm* — Jones Walker LLP

(57) ABSTRACT

A chipless RFID tag system having a transmitter sending an input signal and a tag substrate. An ID generation circuit on the tag relies on microstrip transmission line patterns which are pre-designed to generate a unique code. The ID generating circuit may be designed based upon the transmission line properties, including signal delay, and/or reflection, and/or phase change. The tag may be formed on a flexible substrate having at least one microstrip and the microstrip having a first portion with a first impedance and a second portion with a second impedance different from the first impedance. The tag may further include a microstrip antenna for communication with the transmitter and a receiver system. The tag may also include sensors for detection of desired substances of interest. The system may further include a receiver detecting at least two reflections from an interface of first and second impedances and identifying relative time domain positions of the reflections to one another.

10 Claims, 13 Drawing Sheets

(56) References Cited

U.S. PATENT DOCUMENTS

| | | | |
|---|---|---|---|
| 2003/0043077 | A1 | 3/2003 | Alexopoulos et al. |
| 2003/0048234 | A1 | 3/2003 | Alexopoulos et al. |
| 2005/0093700 | A1* | 5/2005 | Carrender .................. 340/572.8 |
| 2005/0162315 | A1 | 7/2005 | Alexopoulos et al. |
| 2005/0168314 | A1 | 8/2005 | Alexopoulos et al. |
| 2005/0183492 | A1* | 8/2005 | Rao et al. ..................... 73/24.06 |
| 2005/0248455 | A1 | 11/2005 | Pope et al. |
| 2005/0280539 | A1 | 12/2005 | Pettus |
| 2005/0285795 | A1 | 12/2005 | Puente Baliarda et al. |
| 2006/0273904 | A1* | 12/2006 | Funo et al. .................. 340/572.1 |
| 2008/0035740 | A1* | 2/2008 | Tanner .......................... 235/492 |

OTHER PUBLICATIONS

Jui-Han Lu, Chia-Luan Tang, Kin-Lu Wong, "Novel Dual Frequency and Broad-Band Designs of Slot-Loaded Equilateral Triangular Microstrip Antennas", 48 IEEE Transactions on Antennas and Propagations 2000, vol. 7, pp. 1048-1054.

Shyh-Tirng Fang, Kin-Lu Wong, Tzung-Wern Chiou, "Bandwidth Enhancement of Inset-Microstrip-Line-Fed Equilateral-Triangular Microstrip Antenna", 34 Electronics Letters 23 1998, pp. 2184-2186.

Greg H. Huff and Jennifer T. Bernhard, "Integration of Packaged RF MEMS Switches with Radiation Pattern Reconfigurable Square Spiral Microstrip Antennas", 54 IEEE Transactions on Antennas and Propagation 2, 2006.

Montesinos, et al, "The Sierpinski Fractal Bowtie Patch: A Multifracton-Mode Antenna", Antennas and Propagation Society International Symposium, 2002, vol. 4, pp. 542-545.

Parron, et al, "Method of Moments Enhancement Technique for the Analysis of Sierpinski Pre-Fractal Angennas", 51 IEEE Transactions on Antennas and Propagation 8, 2003.

O. Petre and H.G. Kerkhoff, "On-Chip Tap-Delay Measurements for a Digital Delay-Line Used in High-Speed Inter-Chip Data Communications", Proceedings of the 11th Asian Test Symposium (ATS'02), IEEE 2002.

V. Subramanian, et al, "Progress towards development of all printed RFID tags: Materials, Processes and Devices," Proceedings of the IEEE, vol. 93, No. 7, pp. 1130-1338, Jul. 2005.

M.D. Balachandran, S. Shrestha, M. Agarwal, Y. Lvov and K. Varahramyan, "Sn02 Capacitive Sensor Integrated with Microstrip Patch Antenna for Passive Wireless Detection of Ethylene Gas," Electronics Letters, vol. 44, No. 7, Mar. 2008.

J.K. Vemagiri, M.D. Balachandran, M. Agarwal and K. Varahramyan, "Development of Compact Half-Sierpinski Fractal Antenna for RFID Applications," Electronic Letters, vol. 43, No. 22, 2007.

G. Marrocco, "Gain-Optimized Self-Resonant Meander Line Antennas for RFID Applications," IEEE Antennas and Wireless Propagation Letters, vol. 2, pp. 302-305, 2003.

K.V. Seshagiri Rao, Pavel V. Nikitin, and Sander F. Lam, "Antenna Design for UHF RFID Tags: A Review and Practical Application," IEEE Transactions on Antennas and Propagation, vol. 53, No. 12, pp. 3870-3876, 2005.

K.V.S. Rao, "An Overview of Backscattered Radio Frequency Identification System (RFID)," Asia-Pacific Microwave Conference Proceedings, APMC, vol. 3, pp. 746-749, 1999.

S. Mukherjee, "Passive Sensors Using RF Backscatter," Microwave Journal, vol. 47, pp. 96-108, 2004.

C. Hausleitner, A. Pohl, M. Brandl, and F. Seifert, "New Concepts of Wireless Interrogable Passive Sensors Using Nonlinear Components," IEEE International Symposium on Applications of Ferroelectrics, Honolulu, HI, pp. 851-854, 2001.

H.T.Su, Y. Wang, F. Huang, and M.J. Lancaster, "Wide-band Superconducting Microstrip Delay Line," IEEE Transactions on Microwave Theory and Techniques, vol. 52, pp. 2482-2487, 2004.

S.R. Best, "Shunt-stub Line Impedance Matching: A Wave Reflection Analysis Tutorial," IEEE Antennas and Propagation Magazine, vol. 44, pp. 76-86, 2002.

H. A. Wheeler, "Reflection Charts Relating to Impedance Matching," IEEE Transactions on Microwave Theory and Techniques, vol. MTT-32, pp. 1008-1021, 1984.

A. Chamarti and K. Varahramyan, "Transmission Delay Line Based ID Generation Circuit for RFID Applications," IEEE Microwave and Wireless Components Letters, vol. 6, No. 11, pp. 588-590, 2006.

U.K. Dandgey, "Design and Development of a Microstrip Meanderline Antenna for an RFID-Based Passive Wireless Sensor Platform," M.S. Thesis, Louisiana Tech University, Ruston, 2005.

* cited by examiner

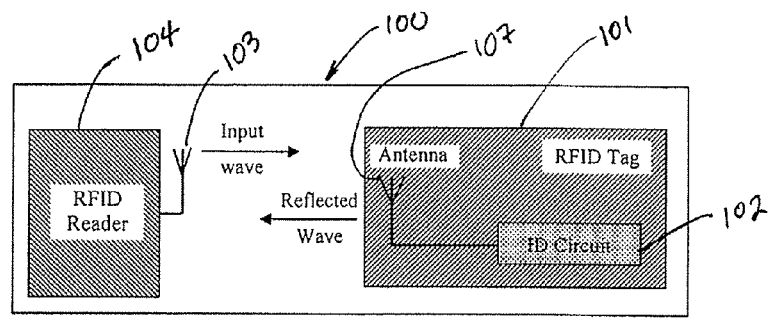
Fig. 1: Schematic diagram of passive RFID system. Prior Art
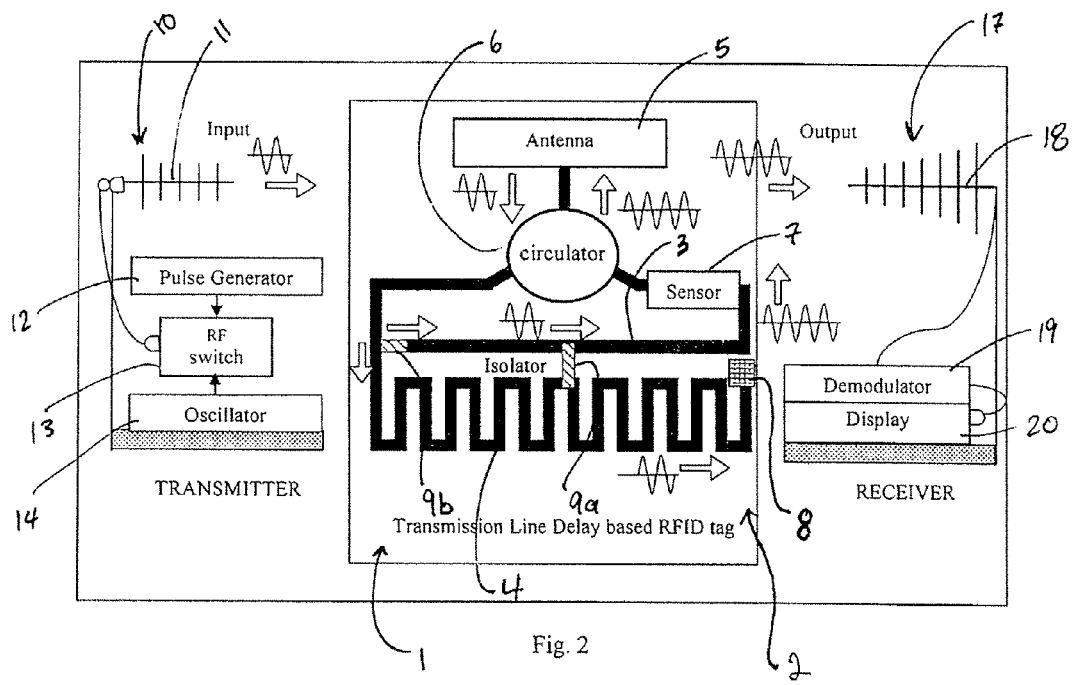
Fig. 2

Figure3: Binary code generation by the superimposition of delayed signals

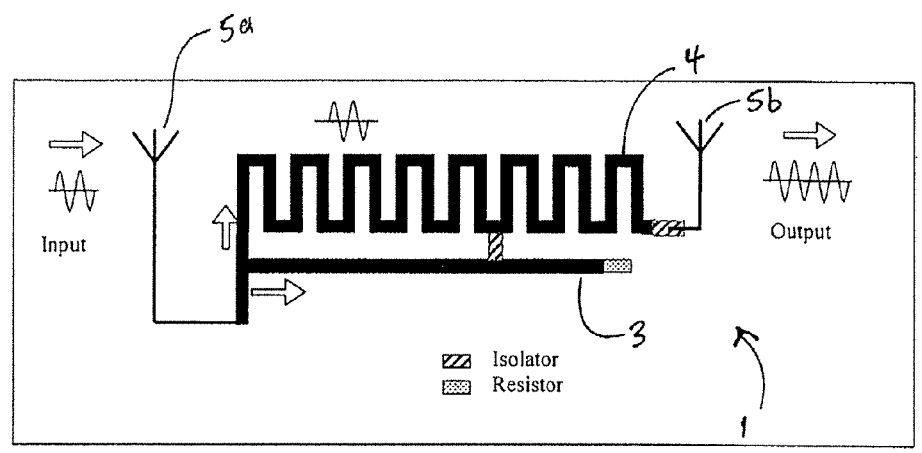
Fig. 4
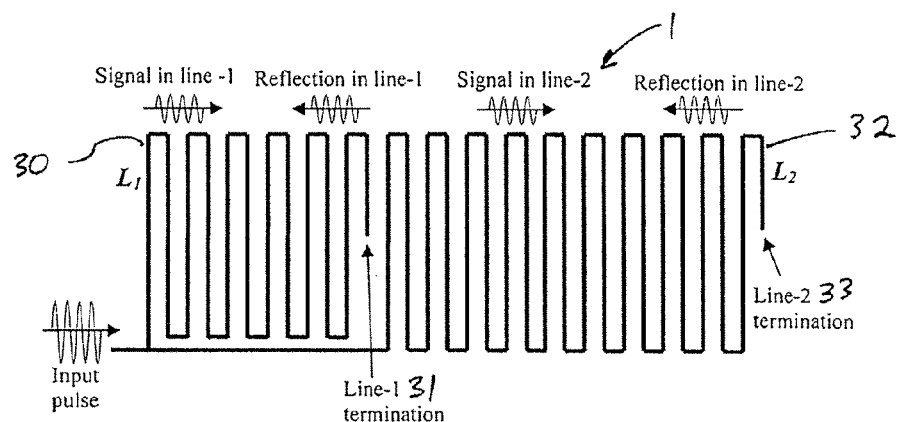
Fig. 5: Pulse reflections in two open terminated transmission lines.

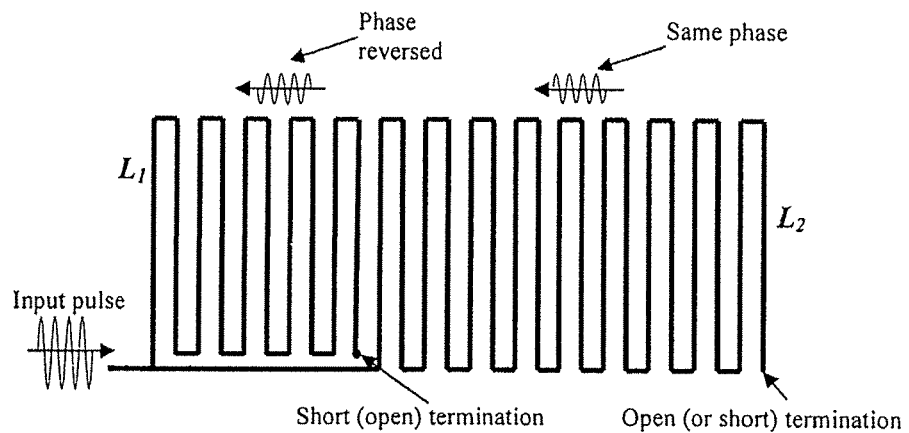
Fig. 9: Phase Modulation Scheme
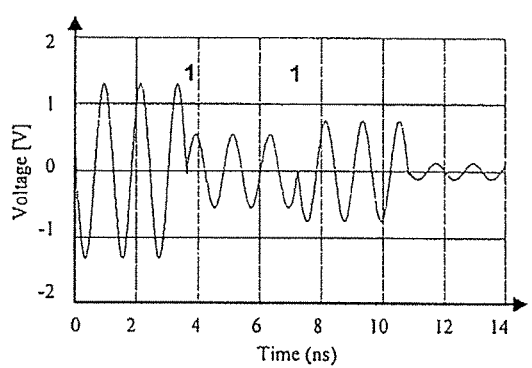
Fig. 10: Reflection pattern representing phase modulated signal pattern.

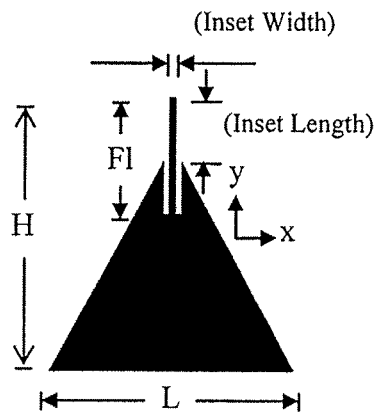
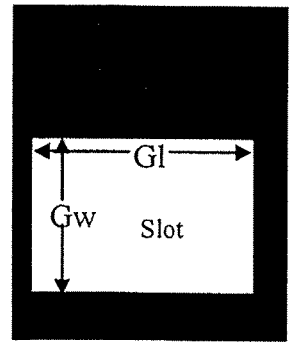
Fig. 12(a)                    Fig. 12(b)
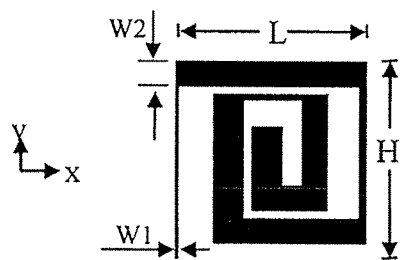
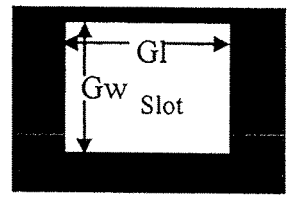
Fig. 13(a)                    Fig. 13(b)
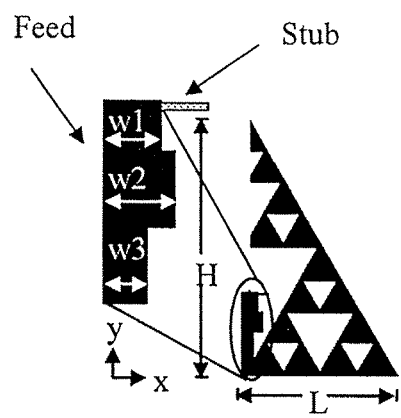
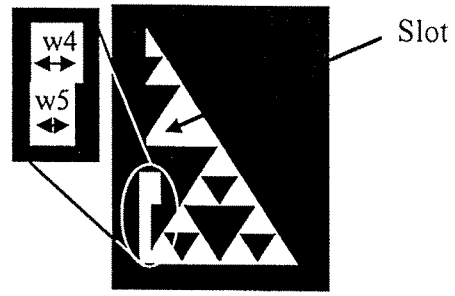
Fig. 14(a)                    Fig. 14(b)

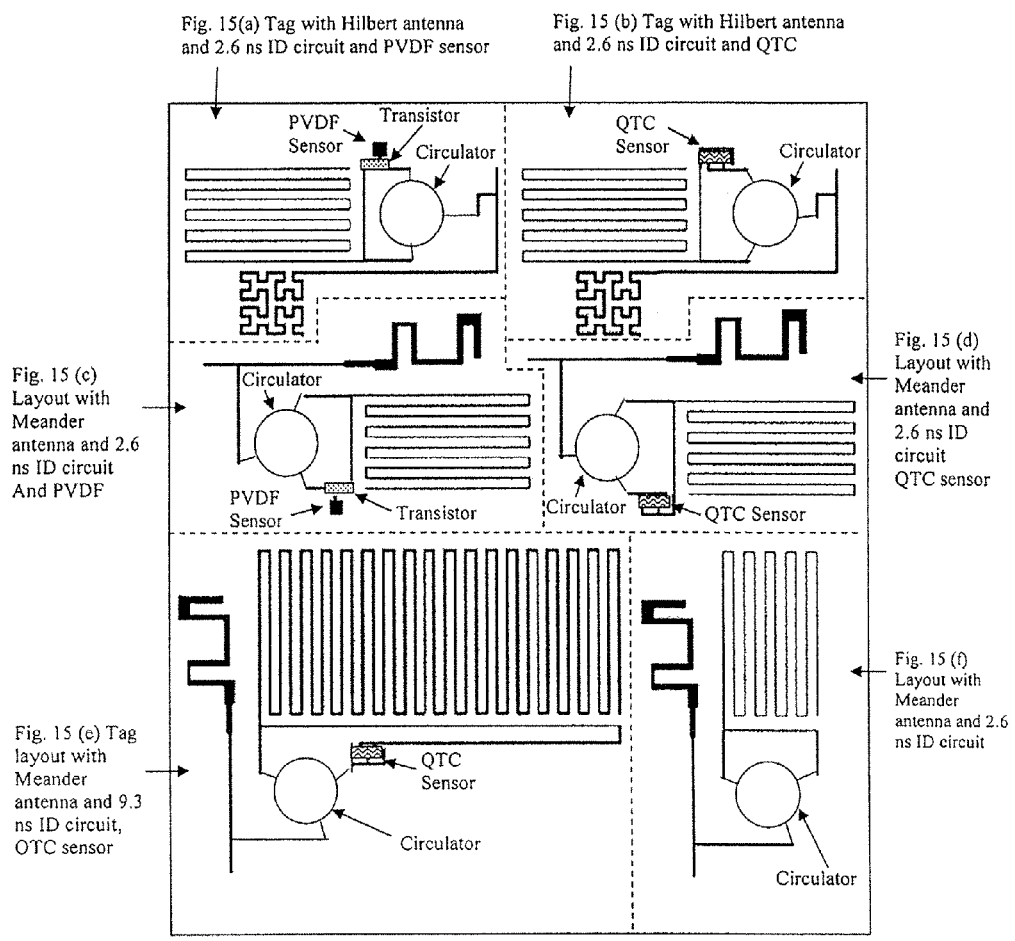
Fig. 15: Mask layout with different RFID and RFID-based sensor configurations

TRANSMISSION DELAY BASED RFID TAG

This application is a continuation-in-part of U.S. application Ser. No. 11/864,159, filed Sep. 28, 2007, which claims the benefit under 35 USC §119(e) of U.S. Provisional Application Ser. No. 60/827,249 filed Sep. 28, 2006, both of which are incorporated by reference herein in their entirety.

This invention was developed at least in part through the use of federal funding from grant no. DARPA N66001-05-8903 and the federal government may retain certain rights in this invention.

FIELD OF INVENTION

The present invention relates broadly to Radio Frequency Identification (RFID) tags and systems for implementing the same. In particular embodiments, the invention relates to passive RFID systems based upon signal propagation delays.

BACKGROUND OF INVENTION

RFID has been a key technology for short range wireless automatic identification. It has been implemented in many recent technologies such as contact-less smart cards, access control, wireless sensing and information collection, industrial automation, ticketing, public transportation, automatic toll collection, animal and product tracking, and medical applications.

Referring to FIG. 1, a typical RFID system 100 consists of two major blocks: an interrogator, such as RFID reader 104, and a remote unit, such as RFID tag 101. The tag has a unique identification code incorporated into the ID circuit 102 and this code becomes associated with the object to which the RFID tag is attached. The RFID reader 104 normally has a transmitter/receiver unit which transmits a signal to and receives a response from the RFID tag. The RFID tag will have an antenna 103 and the RFID reader will have an antenna 107. Unlike barcode technology, an RFID tag can convey more extensive information about the object. The reader sends an interrogation signal and the tag responds with the information stored in it. A RFID system does not require line of sight, and information can be read from comparatively longer distances than bar code scanners. Moreover, multiple tags can be read simultaneously.

RFID tags can be classified as active, reader powered tags (inductive coupling) and fully passive tags. Active tags require power source to operate, therefore are limited by their battery life. Reader powered tags operate by inductive coupling; therefore they are limited by the distance over which they may be read ("read distance"). On the other hand, passive tags consist primarily of an antenna and an ID circuit. They do not require any power supply and work by responding to reader interrogation by changing certain parameters of the interrogation signal. Passive tags tend to be more limited by their read distance and the amount of information which they can convey.

SUMMARY OF SELECTED EMBODIMENTS OF INVENTION

One embodiment of the present invention forms a chipless RFID tag system. The system includes a transmitter sending an input signal and a tag substrate having a first and a second microstrip. The second microstrip is at least twice as long as the first microstrip and has substantially uniform impedance along its length. The system further includes at least one tap positioned between the first and second microstrips allowing one-way transmission of the input signal from the second to the first microstrip.

Another embodiment of the present invention also forms a chipless RFID tag system. This system includes a transmitter sending an input signal and a tag substrate. The tag substrate has at least one microstrip and the microstrip has a first portion with a first impedance and a second portion with a second impedance different from the first impedance. The system further includes a receiver detecting at least two reflections from an interface of the first and second impedances and identifying relative time domain positions of the reflections to one another.

BRIEF DESCRIPTION OF FIGURES

FIG. 1 is a schematic view a basic RFID tag system.

FIG. 2 illustrates one RFID tag embodiment of the present invention.

FIG. 4 illustrates a modification of the RFID tag embodiment seen in FIG. 2.

FIG. 5 illustrates another RFID tag embodiment of the present invention.

FIG. 9 illustrates a phase modulation RFID tag embodiment.

FIG. 10 illustrates a signal pattern from the RFID tag seen in FIG. 9.

FIG. 12 illustrates one triangular patch antenna embodiment.

FIG. 13 illustrates one spiral patch antenna embodiment.

FIG. 14 illustrates one half-Sierpinski patch antenna embodiment.

FIGS. 15a to 15f illustrate various meander and Hilbert antenna embodiments.

DETAILED DESCRIPTION OF SELECTED EMBODIMENTS

Figure 3A:
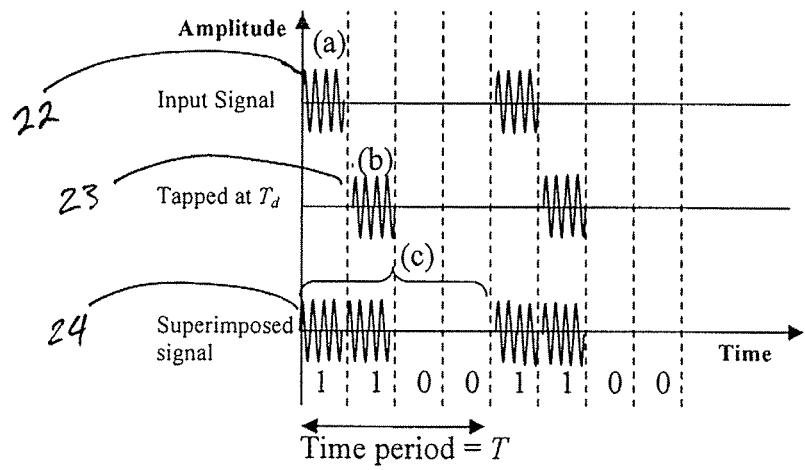
FIGS. 3a to 3c illustrate a signal pattern from the RFID tag seen in FIG. 2.

FIG. 2 is a schematic illustration of one embodiment of the RFID tag system of the present invention. FIG. 2 shows three basic components of the system, transmitter circuit 10, receiver circuit 17, and RFID tag 1. In this particular embodiment, transmitter circuit 10 includes a oscillator 14, an RF switch 13, a pulse generator 12, and a DC supply (not shown). Oscillator 14 supplies a carrier frequency (as a nonlimiting example, at 915 MHz) to the input of RF switch 13. The power needed by RF switch 13 is provided by the DC power supply. The on and off duration of RF switch 13 is controlled by supplying a pulse from pulse generator 12. The output of RF switch 13 is fed to the transmitting antenna 11. This embodiment of transmitter circuit 10 produces a train of sinusoidal signals in a conventional on/off key (OOK) coding. However, the invention is not limited to signals using OOK coding nor the transmitting circuitry seen in FIG. 2. Any conventional or future developed transmitting circuitry could be employed together with any coding scheme which generally accomplishes the functions described below.

This embodiment of receiver circuit 17 includes an antenna 18, a demodulator 19, and a display 20. In the receiver circuit, the demodulator receives the signal from the antenna and demodulates the signal to extract the ID code of the tag, which can then be viewed by the display. The demodulator of this embodiment consists of a low noise amplifier, a local oscillator, a mixer, a band pass filter, an analog to digital converter, and a single board computer. With the carrier signal from the local oscillator, the demodulator demodulates the received signal. The band pass filter blocks high and low frequency components while allowing a low attenuation path for the selected signal. The analog to digital converter converts the analog signal to binary form and feeds it to the single board computer. Based on information loaded in the memory of single board computer, the computer performs the further processing of the signal and decodes the ID code generated by the tag. The ID code generated is displayed on the display system. Although illustrated separately in FIG. 2, it will be understood that transmitter circuit 10 and receiver circuit 17 are the equivalent of the RFID reader 104 seen in FIG. 1. Likewise, there are many ways in which the transmitter/receiver circuitry could be constructed; for example, a single transceiver versus separate transmitter/receiver circuit as suggested by the RFID reader 104, where a single antenna which is shared by both the transmitting and receiving systems is isolated by a circulator. Nor is a display system necessary and the generated code could be fed into another system (e.g., a tracking system or an alarm system) without being physically displayed.

The RFID tag 1 seen in FIG. 2 generally comprises antenna 5, circulator 6, sensor 7, a first conductive microstrip 3 and a second conductive microstrip 4, all positioned on a substrate 2. Microstrips 3 and 4 are generally conductive transmission lines formed on the generally insulating surface of substrate 2. The formation of microstrips 3 and 4 will be described in more detail below, but in the embodiment of FIG. 2, microstrips 3 and 4 have substantially uniform impedance along their lengths and substantially uniform capacitance and inductance properties along their lengths. Microstrip 3 in FIG. 2 is a generally straight trace whose length approximates the width of tag substrate 2, while microstrip 4 is a considerably longer trace which takes on a meandering path in order to accommodate its length on substrate 2. In the embodiment of FIG. 2, microstrip 4 is at least twice as long as microstrip 3. The characteristic impedance, $Z_o$, and the transmission time delay, $T_d$, associated with the microstrips are given by:

$$Z_o = [L/C]^{1/2} \quad (1)$$

$$T_d = [LC]^{1/2} \quad (2)$$

where time delay in the microstrip transmission line is substantially constant per unit length and is distributed substantially uniformly along its length.

Microstrip 4 is shown as terminated by resistor 8, which has an impedance that is substantially equal to the characteristic impedance $Z_o$ of microstrip 4 in order to minimize signal reflections from the terminating end of microstrip 4. FIG. 2 also shows "taps" 9 positioned between microstrips 3 and 4.

In this embodiment, taps 9 are RF isolators such as a model CES 40925MECB000RAB, provided by Murata Electronics North America, Inc. of Smyrna, Ga. The RF isolators are two-port units that allow signals to pass in one direction while providing high isolation for reflected energy in the reverse direction. Isolators are used to allow the delayed signal to flow to the common point or trace in the ID generation circuit and not vice versa. Thus a signal traveling down microstrip 4 will be transmitted to microstrip 3 when the signal encounters tap or isolator 9a. Likewise, an input signal entering microstrip 3 through isolator 9b will not have its reflection (e.g., from sensor component 7) travel back to microstip 4. Naturally, RF isolators are just one form of tap and any conventional or future developed component that can effect such one way signal transmission should be considered within the scope of the present invention.

FIG. 2 also illustrates a circulator 6 and a sensor 7 interconnected with the microstrips 3 and 4. In the most general terms, sensor 7 acts to allow a signal to be transmitted from microstrip 3 to circulator 6 given the presence of a certain condition (e.g., a threshold temperature, presence of a particular compound, etc.) and will be described in greater detail below. Circulator 6 is a passive device that is used to control the propagation of RF signals. RF circulators typically have three or more ports and are used to control the direction of signal flow in a circuit. They allow the signal entering one port to pass to an adjacent port in either a clockwise or counterclockwise direction, but not to any other port. A three port or Y junction circulator is shown in FIG. 2 and the signal flow is normally expressed as 1 to 2, 2 to 3 and 3 to 1. The circulator allows a low attenuation path from port 1 to port 2, and a high attenuation path from port 1 to port 3, thus having the signal going through path 1 to 2, and not to 3 from 1. Subsequently it will allow the signal to go from port 2 to 3 (low attenuation path), but not 2 to 1 (high attenuation path). In one embodiment, the circulator is a MAFRIN0497 available from Richardson Electronics of LaFox, Ill. In operation, the embodiment of FIG. 2 will have transmitter circuit 10 send a short train of sinusoidal waves which may be interpreted as an OOK modulated input signal. The signal propagates very quickly through the shorter microstrip 3, and assuming sensor 7 is activated, the signal will be re-transmitted at antenna 5 and received by receiver circuit 17 (see input signal 22 in FIG. 3a). On the other hand, there will be a delay in the re-transmission of the signal passing through the longer microstrip 4. When the signal reaches tap 9a, the signal is able to travel down the shorter microstrip 3 and be re-transmitted by antenna 5 to receiver circuit 17. Signal 23 in FIG. 3a illustrates the time domain position of this delayed signal relative to the input signal 22. When signal 22 and 23 are superimposed on one another, a signal trace 24 is constructed to represent a binary code. For example, in signal trace 24, a signal of sufficient amplitude in a particular time slot will be considered a "1", while a signal of insufficient amplitude in a particular time slot will be considered a "0." It can be seen that the signal produced by the microstrip arrangement in FIG. 2 produces a four bit binary code of "1 1 0 0."

Figure 3B:
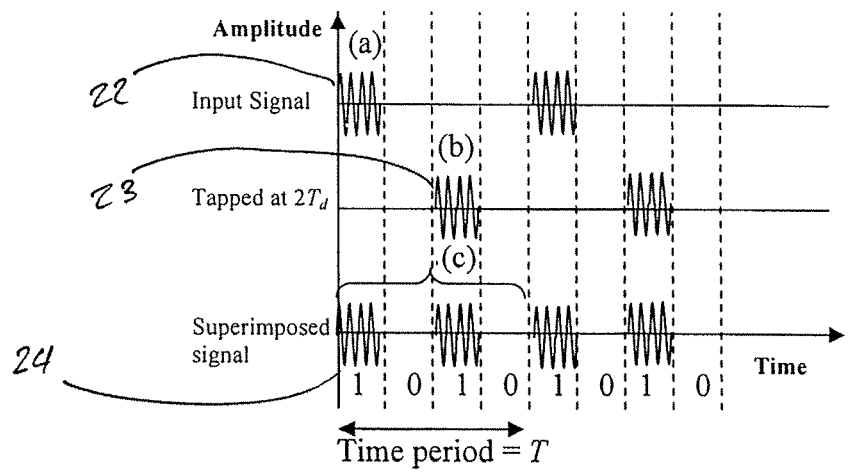
Figure 3C:
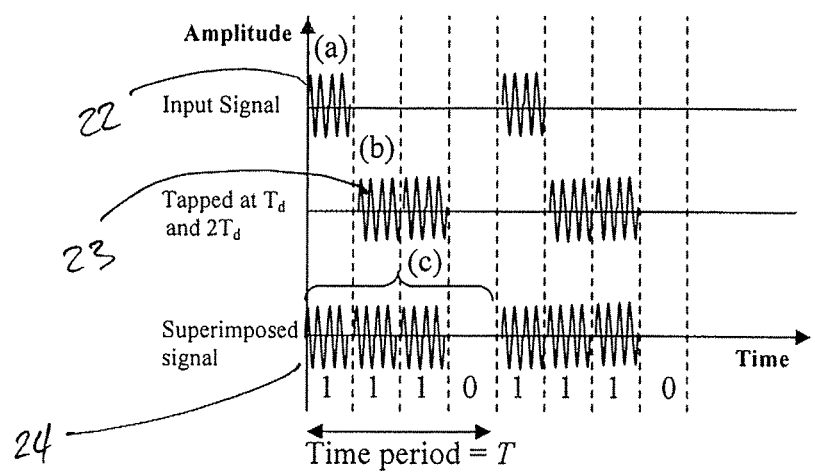

In this embodiment, the code may be altered by altering the position and/or number of taps 9. For example, if tap 9a in FIG. 2 is moved to the right, there would be a greater time delay for signal 23. A signal pattern such as seen in FIG. 3b would result, giving the code "1 0 1 0." Or if a second tap is place to the left of the tap 9a, a signal pattern such as seen in FIG. 3c would result, giving the code "1 1 1 0." In this manner, the code could be altered to any one of 8 combinations. Furthermore, as nonlimiting examples, additional bits could be added to the code by methods such as introducing additional microstrips, by increasing the number of taps, increasing the length of the lines, or reducing the pulse width. The RFID tag of FIG. 2 is considered "chipless" in the sense that no IC chip is utilized to generate a code or other information for transmission to the receiver circuit.

Although FIG. 2 illustrates microstrip 4 as a meandering trace, this is largely done to accommodate the longer overall transmission line on a smaller substrate so the tag has the smallest practical foot print. However, where tag size is not as important, alternate embodiments could include a straight microstrip 4 which is substantially longer than microstrip 3. Another alternative embodiment of RFID tag 1 is seen in FIG. 4. In this embodiment, the circulator 6 and sensor 7 has been eliminated. Rather than a single antenna having a circulator to control when the antenna is transmitting or receiving, the RFID tag 1 in FIG. 4 has a receiving antenna 5a and a separate transmitting antenna 5b. This has the advantage of not requiring a circulator, but also the disadvantage of requiring addition substrate space to accommodate two antennas. Additionally, while the embodiments described above show a common input junction for the two microstrips, alternative embodiments could be fabricated without a common input junction. However, not having a common input junction could require each microstrip to have its own antenna (again a somewhat inefficient use of substrate space).

The sensor 7 in FIG. 2 may be used to detect virtually any condition. For example, the sensor could detect temperature, pressure, light, the presence of a particular compound, or any other condition or state which requires detection. The mechanism of the sensor could likewise be based on a wide range of sensor technologies. As nonlimiting examples, the sensor could be actuated by a change in one or more of the dielectric, electrical, mechanical, chemical, optical, or biological properties of the sensor.

In many embodiments, it is desirable that the sensor consumes low power (e.g., few microwatts) or self-generates the power needed. Solar cells, piezoelectric and pyroelectric materials generate energy and can be used to turn on a switch such as a FET. Materials such as quantum tunneling composites and polyaniline (PANI) change from insulating state to conducting state nonlinearly when the sensed quantity reaches a threshold value. Where no battery is intended in the proposed design, the sensor switch will operate either on its own with self-generated energy or in a passive mode. Quantum Tunneling Composite (QTC), polyvinylidene fluoride (PVDF) and PANI are example materials which can achieve these characteristics.

In certain embodiments, the sensor simply acts as a switch in series with other elements in the RFID tag. In these embodiments, any material that has a non-linear behavior and has the capability to stand alone can be considered for the switch. The sensor switch is an interface between the sensor element and the RF path of the RFID circuit. Non-limiting examples of different types of sensing material employable in the current RFID-based sensors include the QTC, PVDF and PANI materials mentioned above.

For QTC materials, the resistance changes exponentially under pressure making it suitable for use as a switching element for pressure sensing. In QTC materials, the metal particles are separated by a polymer lattice and never come into physical contact. They move very close under pressure and Quantum Tunneling occurs between the metal particles which are now separated by quantum scale distances. Moreover, QTC material can be effectively modeled as an RF resistor switch because it is known to conduct high frequency signals.

Piezoelectric materials such as PVDF generate a charge when a pressure is applied. The charge developed can be converted into a voltage if a capacitor structure is used with PVDF between its electrodes. The charge developed is due to the aligning of the dipoles in the material and this polarization occurs only in the area where pressure is applied. The charge disappears once the pressure is removed and the material acts as any other dielectric material. These materials are not as good as current sources but are quite good voltage sources for use in sensors which require a power source.

Certain types of conductive polymers change their conductivity when they detect fumes such as those that emanate from fruit and vegetable spoilage. Thus, such polymers can be used as a sensor to detect the freshness of the fruit, if appropriately designed. One example of such a conductive polymer is polyaniline.

Still further embodiments of the RFID tag 1 may employ a transmission reflection to generate an identification signal. A pulse signal, reflected from an impedance mismatched transmission line termination, is delayed in time with respect to the input pulse due to the inherent signal propagation delay. In a multiple transmission line system (FIG. 5 discussed below) or step impedance transmission line system (FIG. 7 discussed below), a number of delayed reflected pulses appear at the input terminal due to multiple reflections inside the transmission line. The number of reflections depends on the number of transmission lines or number of impedance steps, while the delay depends on length. By proper design of the transmission line system, reflected pulses can be placed at any desired position to form a predefined signal pattern that represents a unique ID code.

When the impedances of a transmission line and load are not matched, not all the signal power flowing through the transmission line is delivered to the load, and some part is reflected back to the signal input point. The magnitude of the reflection depends on the magnitude of the impedance mismatch, as characterized by the reflection coefficient, $\tau$, where:

$$\tau = \frac{Z_L - Z_T}{Z_L + Z_T} \qquad (3)$$

$$|\tau| = 1 \text{ for } Z_L = 0, \text{ or } Z_L \gg Z_T$$

where, $Z_T$ and $Z_L$ are the transmission line characteristic impedance and load impedance, respectively. If a sinusoidal pulse signal is fed at one end of a transmission line, denoted as the input port, with the other end open, the pulse flows from the input to the open end and gets reflected at the termination. As a result, an attenuated and delayed reflected pulse appears at the input end of the transmission line. The phase of the reflected pulse is the same as the input pulse if $\tau$ is positive, and the phase is opposite if $\tau$ is negative.

One example of a multiple transmission lines ID generation design consists of ground or open terminated transmission lines with common feed point. A ground or open termination results in a reflection coefficient $\tau$ of 1 (which may be considered a 100% impedance mismatch) and when $Z_L=Z_T$, $\tau$ becomes 0 (which may be considered a 0% mismatch in percentage). Sufficient reflections may be obtained by mismatches of less than 100%, i.e., 80% or possibly lesser mismatches (conceivably any range between 20% and 80%) if the detection circuitry is sufficiently sensitive. The number, lengths and terminations of the transmission lines are designed such that the reflection pattern forms a composite signal which follows a predefined digital modulation scheme and represents a unique ID code. The first three reflections, consisting of two primary reflections from the two lines and the third due to superposition of the two secondary reflections, may be used for ID code generation. The relative positions of the reflected pulses depend on the delay and therefore the lengths of the transmission lines. OOK or phase modulated signal patterns may be generated by designing appropriate placement of reflected pulses.

Referring to the example circuit shown in FIG. 5, in this embodiment (with antennas excluded for clarity), the RFID tag 1 comprises at least two microstrips or transmission lines 30 and 32. If a pulse signal is fed to this RFID tag configuration and the two transmission lines are open (or ground) terminated (terminations 31 and 33), the input signal travels in both transmission lines and eventually gets reflected at the terminations 31 and 33, thus producing two delayed reflected pulses at the input port. The time domain positions of the reflected pulses depend on the length of the respective transmission lines. In addition, the reflection from one transmission line (30) serves as the secondary input pulse for the other line (32). Therefore, a secondary reflected pulse follows the two initial reflected pulses. Thereafter, this secondary reflection serves as input for tertiary reflections and so on. The amplitude of the successive reflected pulses diminishes as reflected signals divide at transmission line branches and also due to transmission line losses. The same principles apply for a system of three or more transmission lines.

Figure 6:
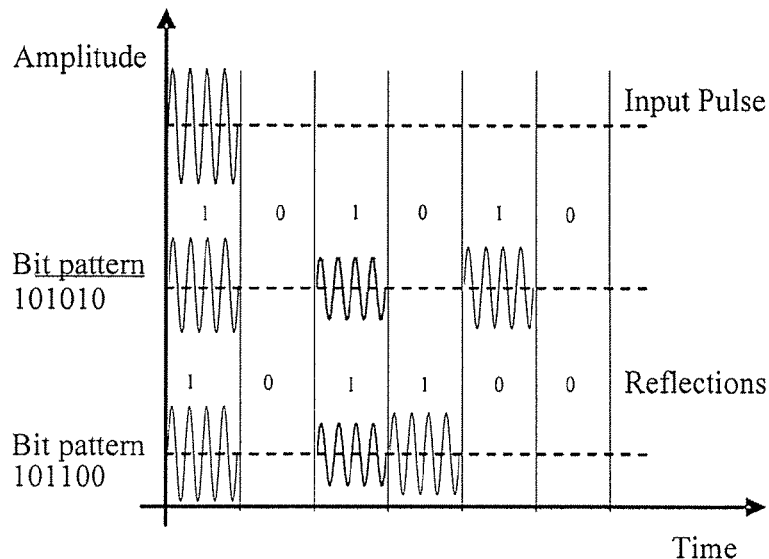
FIG. 6 illustrates a signal pattern from the RFID tag seen in FIG. 5.

Dual transmission line ID circuits such as the FIG. 5 embodiment consist of different combinations of two transmission line lengths to construct OOK modulated signal patterns. FIG. 6 schematically illustrates two different OOK modulated signal patterns representing 101010 and 101100 bit patterns, constructed by placing three reflected pulses in six bit positions. Practically, consecutive reflected pulses are more attenuated than shown in the FIG. 6, and higher order reflections are less useful for code generation, limiting this example to the use of only the first three pulses. However, detection of higher order reflections depends largely on the sensitivity of electronics and the complexity of signal processing systems, particularly relative to future developed electronics and signal processing. Thus, codes generated with higher order reflections are within the scope of the present invention.

The presence of a pulse represents binary 1 and its absence represents binary 0. With this representation, ten different OOK modulated signal patterns, representing ten different ID codes can be constructed. In this embodiment, only three 1s are considered in any sequence for code generation. If n positions are considered with three reflected pulses, taking the first bit as a starting bit, $(n-2)\times(n-1)/2$ bit sequences can be constructed, where n is greater than or equal to the number of reflected pulses (in this example three reflected pulses and six positions). For n positions, to get the maximum number of ID sequences, the number of reflected pulses, here defined as I, is given by I=n/2 when n is even, and it is given by I=((n+1)/2) when n is odd.

For any bit pattern of this embodiment, the length of the first or shorter transmission line ($L_1$) and that of the second or longer line ($L_2$) are given as:

$$L_1 = (i'-i) \times T \times l \quad (4)$$

$$L_2 = (i'-1) \times T \times l \quad (5)$$

where i and i' are the numbers representing the position of the second and the third pulses, respectively. The length of transmission line required for 1 ns reflection delay l is in millimeters, and the bit width T is in nanoseconds (ns). For six bits design, i can take 2 through 5 while i' can take 3 through 6.

Equations (4) and (5) are true for any number of bits, as long as the ID circuit consists of two transmission lines and three pulses are considered. For a 101010 bit pattern, i=3, and i'=5. Taking bit width, T=3.4 ns and l=90 mm/ns, equations (4) and (5) give $L_1$=612 mm and $L_2$=1224 mm. Ansoft planar design of the ID circuit is shown in FIG. 5. For a 101100 bit pattern, lengths of lines $L_1$ and $L_2$ are 306 mm and 918 mm, respectively.

Figure 7:
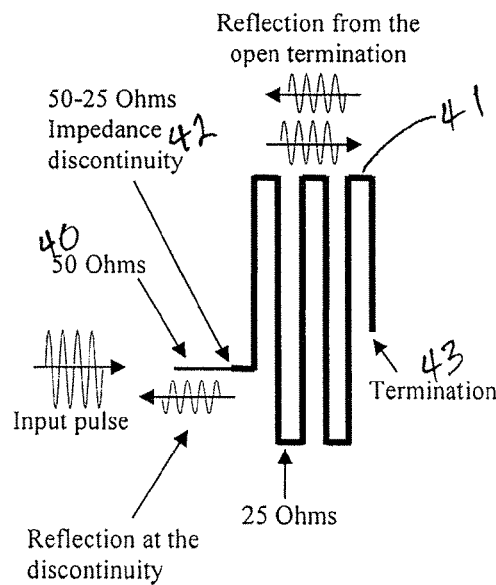
FIG. 7 illustrates a still further RFID tag embodiment of the present invention.

FIG. 7 illustrates the concept of a step impedance tag circuit consisting of a transmission line with a step impedance. Although FIG. 7 only shows one step impedance line, it will be understood that the present invention also includes multiple step impedance lines. With an appropriate selection of transmission line widths and lengths, reflected pulses of proper phase can be placed at any desired position to construct OOK or phase modulated signal patterns.

FIG. 7 shows a step impedance transmission line having a 50 ohms line 40 followed by open (or ground) terminated 25 ohms line 41. If a pulse signal is fed to a step impedance transmission line, as shown in FIG. 7, a third of the signal voltage (i.e., signal power measured in terms of voltage) is reflected at the 50-25 ohms interface 42. The remaining transmitted signal power is finally reflected back from the open termination 43. Some part of backward traveling signal is again reflected at the 25-50 ohms interface. The same phenomenon continues and multiple reflections occur inside the line such that a number of reflected pulses, delayed in time, appear at the input port. As the impedance of a microstrip transmission line for a given substrate depends on its width, a varying impedance microstrip transmission line can be obtained by simply varying width along the length of the line, as suggested in FIG. 7. However, other techniques for varying impedance could be employed, such as varying the thickness or permittivity of the substrate dielectric material at the different line segment. The varying thickness or permittivity can be obtained either by having different materials for different line segments or by doping the substrate material differently. In one embodiment, the impedance mismatch is between about 20% and 40%, but in other embodiments could be between 10% and 90% (or any range there between).

Figure 8:
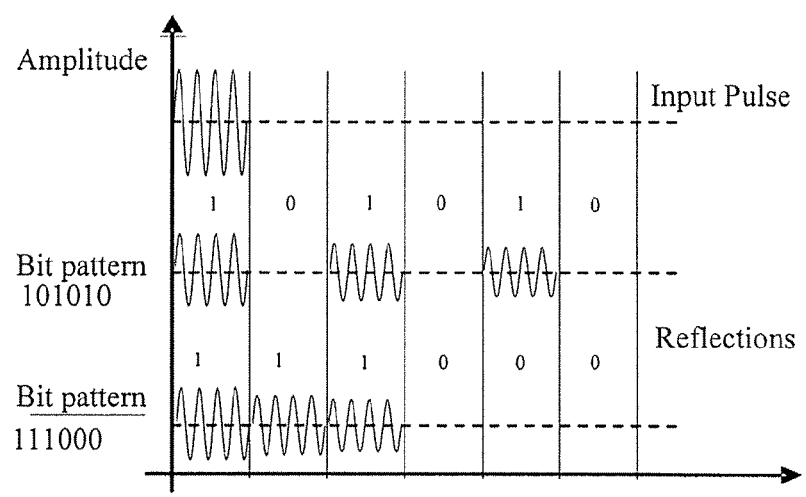
FIG. 8 illustrates a signal pattern from the RFID tag seen in FIG. 7.

One embodiment of these ID circuits is designed by considering the first three reflected pulses. As one example, an ID circuit with a 5 mm long 50 ohm transmission line, followed by a 612 mm long 25 ohm open transmission line, creates a series of reflected pulses separated by 3.4 ns. The reflection pattern represents an OOK modulated 101010 bit pattern with 3.4 ns bit width (see FIG. 8). The design is based on 1 ns delay for a 90 mm long transmission line. As another example, an ID circuit with a 5 mm long 50 ohms line followed by a 306 mm long 25 ohms open transmission line places the first three pulses reflections in a sequence resembling a 111000 bit pattern in a six bit representation.

In the RFID tag embodiment shown in FIG. 9, the second line ($L_2$) is twice as long as first ($L_1$). The first line has short (or open) termination and the second line has an open (short) termination. The reflection from the shorted line is reversed (opposite phase as compared to input) while the reflection from the open line has same phase as the input. The secondary reflection will have an opposite phase if one line is short and another line open, because the reflection travels through both the lines, thus encountering the open termination once, where no phase change occurs, and the short termination once, where the phase is reversed, thereby making overall phase opposite compared to the input. The secondary reflection will have same phase if both the lines are either short or open. The consecutive pulses are delayed in the time domain due to propagation delay in the transmission lines. The length of $L_1$ and $L_2$ are designed such that a succeeding pulse is placed just next to the preceding pulse.

The receiver is designed to detect a phase change in the incoming reflected pulses (i.e., a phase modulation type system). A reverse phase is detected as "1" and the absence of phase change is detected as "0". For the tag embodiment shown in FIG. 9 with the first line shorted and the second line grounded, the phase modulated output pattern will appear as shown in FIG. 10. In this signal trace, it can be seen that there are two phase reversals in the signal pattern, thereby representing a two bit code 11. If the first line were open and second line were ground, it would represent 10, alternatively 01 for both lines shorted, and 00 for both lines open.

As discussed above, the RFID tags typically require at least one antenna. The antenna serves as the transducer between the controlled energy residing within the system and the radiated energy existing in free space. One type of antenna well suited for UHF RFID applications is the non-meandered monopole antenna. Described below are three non-meandered monopole antenna embodiments, each occupying less than 30 cm$^2$ in area. Theses three antennas are the inset-fed triangular patch antenna (FIG. 12), the one arm Archimedes spiral antenna (FIG. 13), and the Half-Sierpinski fractal antenna (FIG. 14). The first two antennas display peak gains of over 2 dBi and the third one has a gain close to 0 dBi. The return-loss of all three antennas is less than −10 dB at the ISM frequency band of 915 MHz. With small length to width ratios, these antennas have certain advantages over the ubiquitous meandered dipole antenna which is often used for RFID applications. In the illustrated embodiment, the antennas are designed for a flexible polyimide platform and can be considered for applications such as the tagging of small-size consumer products.

Figure 11:
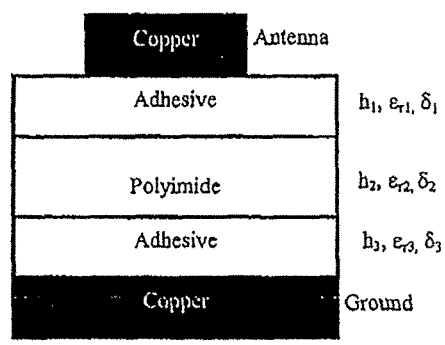
FIG. 11 illustrates a cross-section of one planar antenna substrate.

Presently, meandered antennas are commonly used for UHF RFID applications. However, the generally large dimensional length to width ratio of the meandered antenna structure can make this type of antenna disadvantageous for use in RFID tags requiring small dimensional length to width ratio. Typical length to width ratios of meander antennas currently reported and tested are of the order of 5/1. It would be advantageous to employ an antenna which occupies less surface area than the previously reported meandered dipole antenna, is planar in nature, is developed on a single flexible polyimide substrate, and is designed for high-gain performance. All the antennas described below have a small length to width ratio compared to the meandered dipole antenna. The antennas shown are designed for 915 MHz frequency and having an output impedance of 50 ohm, however, similar antennas may be designed for other frequency and impedance characteristics. One substrate topology employed in the design and fabrication of the antennas is shown in FIG. 11. FIG. 11 illustrates a cross-section of the antenna substrate having copper thickness of 37 µm, $h_1=h_3=25$ µm, $h_2=127$ µm; $\in r_1=\in r_3=3.3$, $\in r_2=3.5$; $\delta_1=\delta_3=0.027$, $\delta_2=0.008$.

FIG. 12 illustrates an inset-fed triangular patch antenna designed on the substrate seen in FIG. 11. The impedance of the antenna is matched to 50 ohms by adjusting the inset-length (Il) and width (Iw). To increase the gain of the antenna, a slot is created on the ground plane (the ground layer seen in FIG. 11) defined by Gl×Gw (length and width). The dimensions of the slot are varied to increase the gain of the antenna and the optimum slot dimensions would give maximum gain for the given antenna (i.e., any other larger or smaller dimension of the slot would result in lower gain). The optimum slot dimensions may be determined by altering the dimensions in software simulations until the maximum gain is reached. The surface area occupied by this antenna is 15 cm$^2$. In this embodiment of the triangular patch antenna, the dimensions are H=5.54 cm, L=5.34 cm, Fl=2.33 cm, Iw=0.15 cm, Il=1.07 cm, Gl=6.09 cm, Gw=5.19 cm.

FIG. 13 illustrates an eleven-segment single arm Archimedes spiral developed for the platform seen in FIG. 11. The widths of the spiral arm in this example are varied to match the antenna to 50 ohms impedance. A slot Gl×Gw is introduced in the ground plane to optimize the gain of the antenna. FIG. 13(a) shows the design of the spiral patch antenna and FIG. 13(b) shows the patch-aligned underlying ground layer. Example dimensions for one embodiment of the spiral patch could be w1=1 mm; w2=8 mm; w3=2 mm; w4=8 mm; w5=8 mm; w6=2 mm; w7=7 mm; w8=8 mm; w9=8 mm (w3 to w8 are not labeled in FIG. 13(a), but are the widths of the successive spiral arms moving inward); H=6.0 cm, L=5.0 cm, Gl=5.4 cm, Gw=5.7 cm. The surface area occupied by this antenna is approximately 30 cm$^2$.

FIGS. 14(a) and 14(b) illustrate a Half-Sierpinski antenna which is derived from the Sierpinski Monopole to capture the multi-resonant properties of the Sierpinski monopole at a smaller size than the parent version. The surface area occupied by this example antenna is 9.5 cm$^2$. The impedance of this example antenna is matched to 50 ohms by varying the widths of the feed of the antenna and by introducing a stub which is grounded at one end at the feed of the antenna. The stub is grounded at one end to reduce the length of the stub that is to be added to the antenna to match the impedance of the antenna to 50 ohms. The width of the stub is 0.4 mm and the length is about 2 mm. The gain of the antenna is optimized by modifying the slot size in the ground plane. Example dimensions for one embodiment of the patch and ground layouts (FIGS. 14(a) and 14(b)) are H=5.7 cm, L=3.3 cm, w1=0.25 cm, w2=0.35 cm, w3=0.15 cm, w4=0.35 cm, w5=0.15 cm.

Although the above describes three antenna designs well suited to RFID tags, many other antennas may be employed in the present invention, nonlimiting examples of which include Meander and Hilbert antennas such as seen in FIG. 15. FIG. 15(a) shows a 2.6 ns ID circuit with a Hilbert antenna and a PVDF sensor. FIG. 15(b) shows a 2.6 ns ID circuit with a Hilbert antenna and a QTC sensor. FIG. 15(b) shows a 2.6 ns ID circuit with a Hilbert antenna and a QTC sensor. FIG. 15(c) shows a 2.6 ns ID circuit with a meander antenna and a PVDF sensor. FIG. 15(d) shows a 2.6 ns ID circuit with a meander antenna and a QTC sensor. FIG. 15(e) shows a 9.3 as ID circuit with a meander antenna and a QTC sensor. FIG. 15(f) shows a 2.6 ns ID circuit with a meander antenna (but no sensor). Moreover, the present invention could include any other conventional or future developed antennas fulfilling the required functions of the RFID tags described above.

Many different techniques may be employed to manufacture the RFID tags described above. In one embodiment of the present invention, the RFID tags will be formed on a flexible substrate. Examples of such flexible substrates include polyimides, polyesters, and polyethylene-tereptphalates (PET). Preferred substrate materials should have reasonable thermal stability (e.g., at least 150-250° C. without physical deformation), suitable surface roughness to allow adhesion of coatings, and sufficient chemical inertness such that the deposition processes do not damage the substrate. A nonlimiting example of a suitable polyimide substrate is Kapton VN available from E. I. du Pont de Nemours and Company.

Suitable conducting materials for the flexible electronic circuits contemplated may include (but are not limited to) metals, metallic nanoparticle inks and conductive polymers. These materials may used to fabricate antennas, wireless components, interconnects, contacts and devices such as planar inductors and capacitors. In some embodiments, conventional inkjet printers may be used to create the desired circuit pattern. Gold and silver nanoparticle inks are alternatives but are expensive and their printing may be time consuming. Conductive polymers are inexpensive but their printing is also comparatively time consuming. Physical vapor deposition (PVD) is a process which gives good quality metal patterns, but it is also comparatively expensive. Finally, metals such as copper may be deposited electrolessly which is comparatively simple and inexpensive as compared to processes listed above. However, any of the above processes (or other processes) may be possible alternatives if their time and cost factors meet the particular design requirements under consideration.

Where required for circuit design, semiconducting polymers may used for the channel material of FETs and in the fabrication of devices such as diodes. P-type materials such as doped polypyrrole or PEDOT doped with PSS are good candidates certain embodiments as they are stable in atmospheric conditions and are commercially available at low cost. These polymers can also be printed using a commercial desktop type printer.

Where necessary to have insulating materials, many compounds, including polyimides and epoxies, are available which may be either spin-coated, dip-coated, or spray-coated onto flexible substrates and are well known for their insulating properties. They may be cured thermally or with UV light. As one nonlimiting example, a polyimide such as PI7858G available in semiliquid or liquid form from HD Microsystems of Parlin, N.J.) may be used as an insulating intermediate layer in the microfabrication of devices and ultra fast epoxy encapsulant (e.g., Dymax 9008 from Dymax Corporation of Torrington, Conn.) is an acceptable general purpose product for encapsulating and sealing electronic components for chip-on-flex applications. Chip-on-flex (COF) packaging provides an alternative to reduce the packaging interconnect required in many applications. COF has high bending strength and is thus very useful for applications where the bending of the circuit is required in the assembly of a device.

In one embodiment, circuit patterns may be formed by a xerographic process. If a laser printer is used to pattern a transparency, the toner material acts as an insulating shadow mask on the transparency. Metal or conducting polymers may be deposited on the patterned transparencies using different deposition techniques and the toner may be removed later using sonication in acetone or toluene similar to a conventional lift-off technique. Printer resolution may be an important consideration in determining the design approach for circuit patterning using xerographic methods. A laser printer's resolution is given in dots per inch (dpi). A high end printer can have a resolution of 2400×2400 dpi (or better) which translates into each dot being a minimum size of 10.58 μm.

In another embodiment, circuit patterns may be formed by inkjet printing. Some water-based conducting polymer solutions or solutions that are relatively neutral (a pH of about 7) can be printed directly onto the transparencies by using deskjet printers and loading clean ink cartridges with these polymer solutions. In certain embodiments, polymers such as, PEDOT/PSS and polypyrrole (PPy) may be made highly aqueous (e.g., about 10 to 100 mg/ml) in order to obtain a uniform continuous printable pattern on a Kapton 500VN substrate. Multiple layers of the patterned ink typically improve the electrical performance of the circuit.

In a still further embodiment, electroless copper deposition offers a low-cost option to sputtering and physical vapor deposition (PVD). Usually, electroless copper is used as a seed layer followed by electrolytic deposition of copper, but recent improvements also allow electroless copper to be used directly as the interconnecting metal in flexible electronics.

The quality of the electroless deposition is affected by many variables, including bath conditions such as continuous $N_2$ bubbling, mechanical agitation, and substrate type. Additionally, surface treatments, including activation and acceleration, may be advisable for many commercially available substrates such as PETs and polyimides.

In one embodiment, adhesion of copper to a polyimide substrate (Kapton 500VN) may be significantly increased by electroless deposition of a seed layer of copper on the polyimide substrate, heating at 400° C. for 30 seconds, etching the copper away using an $HNO_3$ solution (leaving only some nuclei spots of a few microns to enhance the electroless deposition of copper in the next stage), and then using the substrate for final deposition of copper.

Certain embodiments may also use activation and acceleration of the substrates for further deposition of copper. The activation step generally involves the coating of the non-catalytic surface with catalytic colloidal particles. In one example, the substrate (e.g., a polyimide sheet) is exposed to a palladium and tin containing solution. The acceleration step generally involves exposure to an accelerator solution consisting of an organic or mineral acid which removes the excess tin from the non-patterned areas while leaving the palladium sites intact for the deposition of the electroless copper. The substrate should be immersed in the accelerator solution for approximately 1 to 3 minutes. During electroless copper deposition, conditions should be carefully controlled such as: timely filtering of the bath solution and adjustment of the pH; accurate maintenance of operating temperature; uniform nitrogen bubbling in order to avoid blistering; and continuous agitation of the bath solution.

Conventional spraying devices (e.g., a bottom feed air-brush with a 0.5 mm needle) may be used for manually spray coating liquid polyimide onto substrates in order to control the surface properties of the substrate for proper adhesion of the toner when employing xerographic printing techniques. The quality of the coated layer may be controlled by varying the viscosity of the polyimide (e.g., by adding NMP), selecting the nozzle size, and selecting the angle of the spray. Several coats (e.g., five or more) may required to cover the entire surface of the substrate with out leaving gaps. A hot air blower may be used between consecutive coats to partially evaporate any lingering solvent. A final thermal treatment of the spray coated substrate in a vacuum thermal oven is useful for evaporating NMP.

In certain circuit designs, grounding may be required for some of the components of the RFID tag. In such instances, the wireless tag circuit may be grounded to the bottom metallic layer through a conducting via. In one embodiment, a conventional Plate-Through-Hole Process is used and employs a ready-to-use electroless bath (e.g., Cuprothick 84 produced by Alfachimici S.p.A. of Moncalieri, Italy). A needle may be used to manually drill a hole approximately 400 μm in diameter and the hole is electroless copper plated for one minute. The thickness of the plated copper may be increased by increasing the deposition time.

Figure 16:
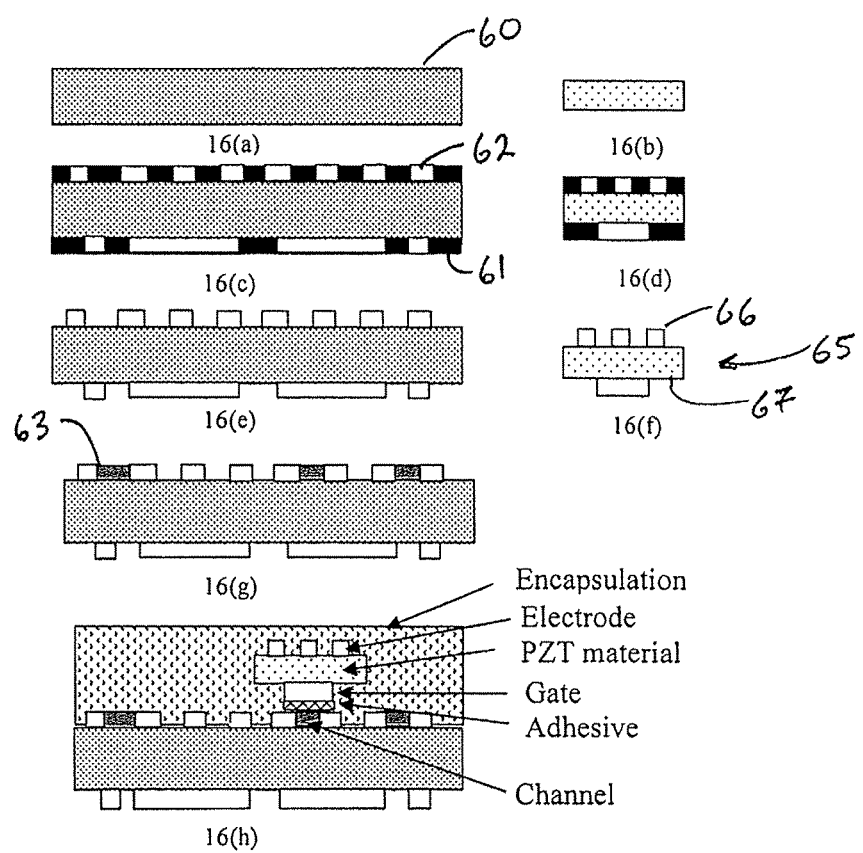
FIGS. 16(a) to 16(h) illustrate a series of process steps for creating one embodiment of an RFID circuit.

One example of the steps performed in a fabrication process similar to that outline above is illustrated in FIG. 16. A Kapton VN500 film 60 is taken as the flexible substrate (FIG. 16(a)) and is loaded into a conventional laser printer. The layout of the tag may be designed in simulation programs such as Coventor or Ansoft, and then converted into a pdf format for printing purposes. Depending on the design, the layout is printed on one or both the sides of the substrate using a desk top laser-jet printer. The substrate, with the toner acting as shadow mask, is then dipped in activation and acceleration solutions for three minutes each and then copper may be deposited using a conventional ready-to-use electroless bath (e.g., Cuprothick 84). FIG. 16(c) shows the copper patterns 62 on the toner covered substrate. The toner material 61 may be removed using ultrasonic vibrations in acetone or toluene. The substrate containing the copper patterns (FIG. 16(e)) may now be loaded into an inkjet printer to deposit a PEDOT/PSS layer 63 for the channel material of the switch (FIG. 16(g)). If required by the particular circuit design, diodes may be printed on the layout in a similar way. The process steps depicted above may also be used to metalize and pattern a piezoelectric polymer sensor material 67 with copper electrodes 66 to form a sensor element 65 for integration with the organic switch of the wireless tag (FIGS. 16(b), (d), and (f)). The sensor element 65 may be attached to the channel region of the switch by using an adhesive that acts as the gate insulation material (FIG. 16(h)). Using a transparent sensor material (e.g., polyvinylidene fluoride (PVDF)) and an adhesive allows the gate to be visually aligned with the channel with sufficient accuracy. Processing temperatures should taken into consideration in designing the fabrication process hierarchy. The materials should be chosen such that there is no significant mismatch in the thermal expansion coefficients which, if large, may result in poor device reliability. A polyimide spray coating can be administered for protection and packaging. Alternatively, a UV cured epoxy encapsulant provides reliable protection and packaging of the final tag device.

Figure 17:
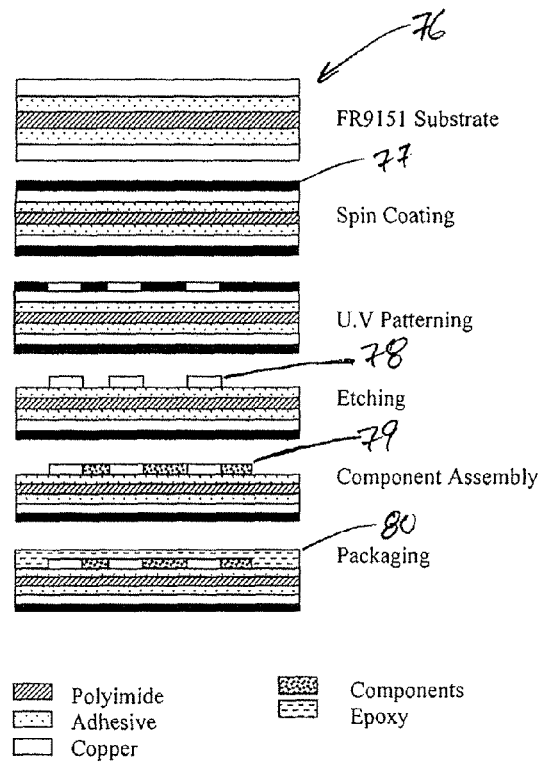
FIGS. 17(a) to 17(f) illustrate a series of process steps for creating another embodiment of an RFID circuit.

Although the above embodiments describe comparatively low-cost methods of fabricating RFID tags on flexible substrates, the present invention includes other methods of fabricating RFID tags. One such alternative method employs conventional silicon-based processes well established in the micro-chip industry. FIG. 17 shows a schematic diagram of one such process and the hierarchy for making RFID tags and RFID-based sensors.

Referring to FIG. 17(a), a suitable starting substrate is a double sided copper clad polyimide substrate (such as FR9151 from Dupont Pyralux) which is thermally stable up to 300° C., has high dimensional stability, and has good peel strength. The tag's layout may be designed using Ansoft Designer simulation software and pdf format softcopies of the masks printed either by using a high resolution printer (e.g., a film mask using Linotronics 330 with a 4000 dpi resolution) or glass mask made using an optical lithography process, (e.g., laser writing or a UV stepper, which part of a conventional lithography process capable of creating millions of microscopic patterns on the surface of photoresist coated on glass). Using these masks, the substrate 76 is patterned by a photolithography process that includes spin coating of a conventional photoresist 77 (e.g., PR1813 photoresist from Shipley Company of Marlborough, Mass.), UV curing, and Ferric Chloride (MG Chemicals) etching for 20 minutes. Depending on the design layout, either both sides or one side may be patterned (FIG. 17(c)), leaving elements such as copper traces 78 (FIG. 17(d)). Components 79 such as resistors, diodes and FETs may be attached using conductive silver epoxy (Chemtronics Inc), by soldering, or any other suitable means (FIG. 17(e)). In the case of the RFID-based sensors, the sensor material is placed on the sensor layout using insulating glue. UV curable epoxy 80 may be used as an encapsulant and prevents oxidation of the copper (FIG. 17(f)). UV curing eliminates heating during the packaging of the tag which could cause thermal damage to other components and layers. Wherever necessary, grounding of the components may be achieved by manually drilling a hole and filling it with conductive epoxy to make connection to the bottom ground plane layer.

Although several embodiments described above are designed by simply using conductive lines on the substrate, in certain alternative embodiments, off-the-shelf components may be used for realizing the RFID concept and the tag.

Figure 19:
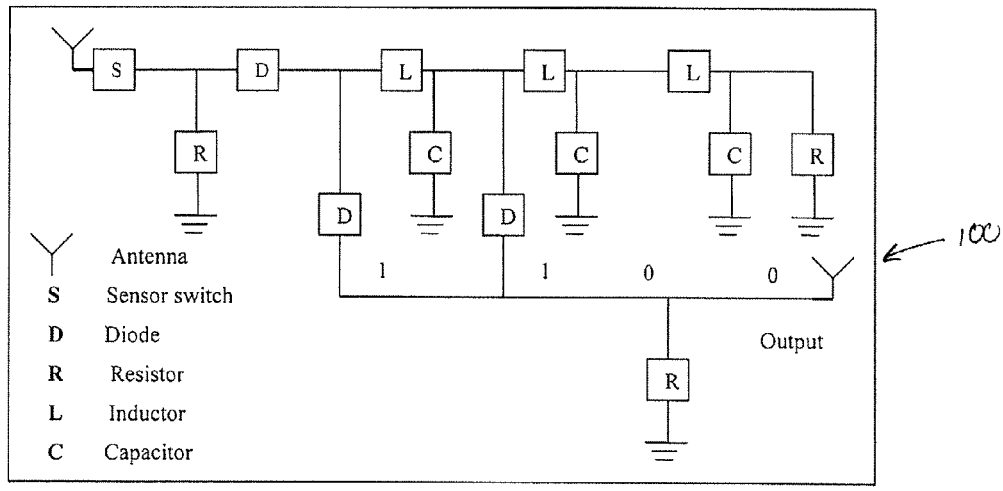
FIG. 19 is a schematic of an LC delay line circuit.
Figure 20:
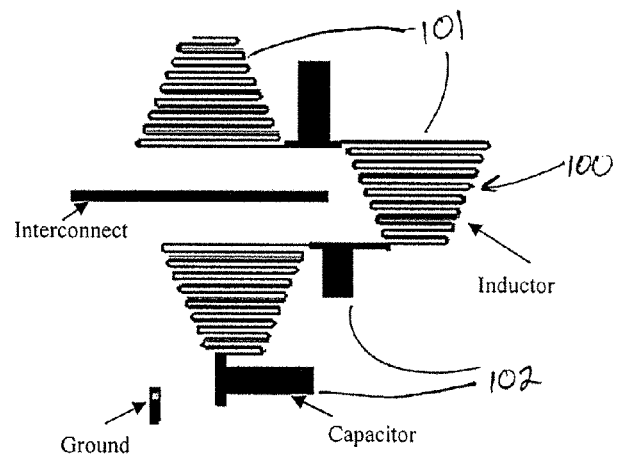
FIG. 20 illustrates LC components created with microstrips.

Although earlier embodiments have described RFID circuits created using different length microstrips to create a readable signal delay, other embodiments may use an inductor/capacitor (LC) type circuit to create the signal delay. An RFID circuit based on the LC delay line concept may have passive elements such as, resistors, inductors, capacitors and diodes. Each set of LC elements is designed to produce a delay corresponding to a bit width. FIG. 19 schematically shows a delay line circuit 100 having three LC elements. In addition to the capacitors, inductors, and resistors, the circuit may include diodes, an antenna(s) such as described above, and a sensor such as described above.

Where possible, planar circuit elements are preferred in producing an LC delay line RFID tag, especially if the tag is to be produced on a flexible substrate and using the printer techniques described above. To create inductors, one embodiment employs a meandering microstrip line 101 of conducting material such as seen in FIG. 20. A capacitor is created by forming "plates" 102 (only the top plate being seen in FIG. 20) which are separated by a dielectric material in the circuit substrate. Resistors may be created by placing a resistor material in the microstrip line. One example of a suitable resistor material is the PEDOT/PSS layering described above. If diodes are necessary for the circuit design, discrete, off-the-shelf diode components may used since diode effects can be more difficult to produce with microstrip designs. Further embodiments of LC delay line RFID circuits include those shown in "Design And Development Of An ID Generation Circuit For Low-Cost Passive RFID-Based Applications," master's thesis of Sireesha Ramisetti, La Tech University, November 2005, which is incorporated by reference herein in its entirety.

A further embodiment of the present invention involves a passive wireless sensor strip. As suggested in FIG. 18(a), the sensor strip generally comprises a sensor substrate 86, a strip antenna 87 positioned on the substrate, and a passive sensor device 88 positioned on the substrate 86 and connected to the strip antenna 87. In preferred embodiments, the passive sensor device is capable of altering the reflection characteristics of the antenna when exposed to a target condition.

In one embodiment of the passive sensor strip 85, the substrate 86 will be a flexible material, including as nonlimiting examples, the flexible substrates outlined above. The strip antenna 87 may be one of the antenna's described above or it may be any other antenna formed by applying a layer of conductive material to the substrate in a shape that allows acceptable signal reception. In one example, the conductive layer forming the antenna will be less than 500 um thick and more preferably 10 um to 50 um thick.

Figures 18A, 18B:
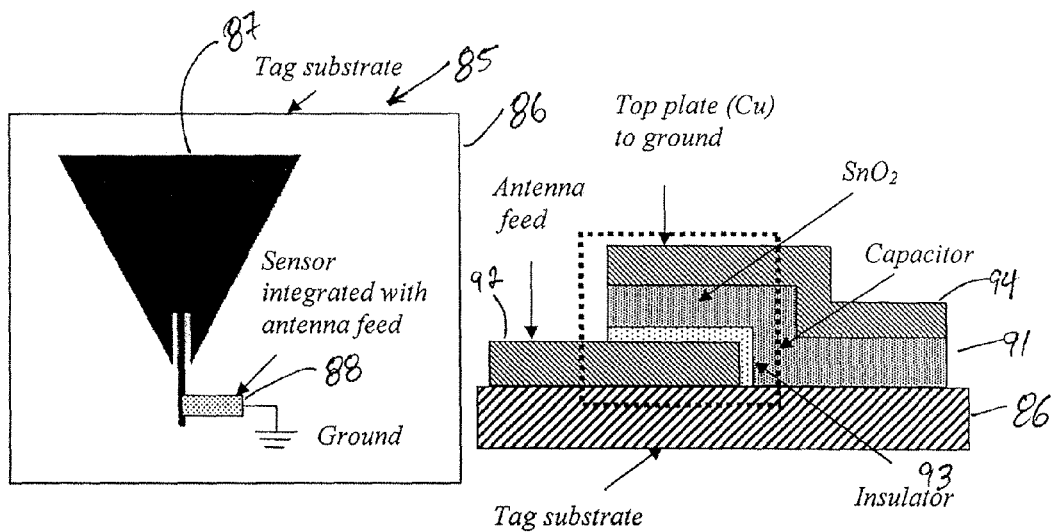
FIGS. 18(a) and 18(b) illustrate an embodiment of a sensor integrated directly with an antenna.

The sensor device 88 may be a device which is capable of altering the reflection characteristics of the antenna when the sensor is exposed to a target condition. Examples of sensor types and target conditions may be those discussed above or any other conventional or future developed sensor type. In one preferred embodiment, the sensor device operates by changing capacitance upon exposure to the target condition. In one example, the sensor device 88 is a nanoassembled capacitor sensor (1-10 pF) integrated with 915 MHz passive microstrip triangular patch antenna 87 as shown in FIG. 18(a) which has been formed on a flexible polyimide sheet. This particular capacitor sensor is configured to detect ethylene by employing tin oxide ($SnO_2$) nanoparticles coated on a conducting layer.

Tin dioxide is an n-type semiconductor consisting of a depletion layer and conduction layer. In air, oxygen is absorbed and a depletion layer (depleted of e) consisting of $O^-$ ionic species is formed. As more oxygen is absorbed the depletion layer becomes thicker and the conduction layer becomes thinner. When a combustible gas like ethylene is encountered, the depleted electrons are replenished on the $SnO_2$ surface and more of the conduction layer is formed. The change in the thickness of conduction and depletion region causes a change in the capacitance. The formation of $e^-$ and reduction of $O^-$ ions is proportional to the increase in ethylene concentration.

Even a small change in capacitance due to the presence of ethylene may shift the resonant frequency of the antenna. The shift in resonant frequency increases the VSWR (voltage standing wave ratio) at the detecting frequency of 915 MHz. The increase in VSWR affects the reflection coefficient as shown in equation (6) which in turn changes the return loss at the measuring frequency of 915 MHz (equation (7)).

$$\text{Reflection coefficient } |\tau| = \frac{|VSWR - 1|}{|VSWR + 1|} \quad (6)$$

$$\text{Return Loss} = -20 \log|\tau| \quad (7)$$

Although 915 MHz is used in this embodiment, a wide range of frequencies can be used if not limited by governmental regulations. However, at very low frequencies the size requirements for the antenna become much larger and at very high frequencies, the attenuation and circuit requirements become more stringent. In many RFID applications, a range starting from some hundred MHz to a few GHz may be preferred (e.g., 300 MHz to 3 GHz, approximately the UHF band).

When ethylene is present, the capacitance of the sensor decreases and the change is detected by the wireless measurement of return loss at 915 MHz. The sensor 88 is preferably integrated at the end of the feed of the triangular antenna 87 as the radiation pattern may be significantly affected even by a small change in capacitance.

One method of manufacturing this capacitive sensor includes forming the sensing dielectric layer of $SnO_2$ colloids (for example, a Nyacol Colloidal Tin 15 nm particle size and counter ion concentration of 0.23% $NH_3$) at room temperature using low cost dip coating techniques. The triangular microstrip patch antenna is fabricated using standard photolithography process on a flexible polyimide substrate 86. As suggested by FIG. 18(*b*), the feed of the antenna forms the bottom plate 92 of the capacitive sensor. Cellulose acetate is also dip coated as the insulating layer 93 and dried at room temperature. The coated nanoorganized sensitive layers 91 have a thickness of about 1000 nm and can be further reduced down to 500 nm which is much less than the traditionally used coating technologies. Lastly, the top copper plate 94 may be deposited by E-beam evaporation and is connected to the antenna ground.

There are many other embodiments the invention could take. One example embodiment includes a chipless RFID tag comprising a tag substrate having at least first and second microstrips. Each of the microstrips has (a) an impedance mismatch of at least about 80% at the microstrip's termination, wherein the mismatch is determined by:

$$\left| \frac{Z_L - Z_T}{Z_L + Z_T} \right|$$

where $Z_L$ and $Z_T$ are the impedance associated with the transmission line and its termination, respectively; and (b) a different length from the other microstrip. As further alternatives, the second microstrip may be at least twice as long as the first microstrip; or the microstrips may be meandering; or the different lengths of the microstrips may cause signal reflections to have a sufficient time period between the reflections to differentiate separate reflections; or the microstrips may have either a substantially open or a substantially grounded termination; or the different lengths of the microstrips may cause the reflections to form a detectable on/off pattern of at least four bits; or the length of the first microstrip (L1) and that of the second microstrip (L2) may be approximately equal to:

$$L1 = (i'-i) \times T \times l$$

$$L2 = (i-1) \times T \times l$$

where i and i' are the position of second and third pulses, respectively; l is the length of transmission line required for 1 ns reflection delay, and T is the bit width in the time domain.

A still further alternative includes a passive wireless sensor strip comprising a passive sensor device fabricated on the substrate and connected to the strip antenna, the passive sensor device altering the reflection characteristics of the antenna when exposed to a target condition. The sensor device may comprise a layer of semi-conductor material positioned between two conducting layers and an antenna lead comprising one conducting layer.

Another example embodiment includes a passive sensor device fabricated on a substrate and connected to a strip antenna with the passive sensor device altering the reflection characteristics of the antenna when exposed to a target condition. The sensor device may comprise a layer of semi-conductor material positioned between two conducting layers; or the sensor substrate may be flexible and the strip antenna comprised of a conductive layer less than 500 μm thick formed on the substrate.

A further example embodiment includes (a) a flexible substrate; (b) a first elongated conductive microstrip formed on the substrate; and (c) a second elongated conductive microstrip formed on the substrate, wherein the second microstrip has a meandering path which is at least twice the length of the first microstrip. Additionally, the first and second microstrips may have a common input port; or the delay in the microstrips may be substantially constant per unit length; or the common port may be connected to an antenna.

An example embodiment may include a tag substrate having at least one microstrip with the microstrip having a first portion with a first impedance and a second portion with a second impedance different from the first impedance. The impedance mismatch between the first and second line may be equal to:

$$\left| \frac{Z_1 - Z_2}{Z_1 + Z_2} \right|$$

where $Z_1$ and $Z_2$ are the impedance associated with the first and second lines, respectively and the impedance mismatch between the first and second lines is between about 20% and about 40%; or the tag may include a sensor which selectively allows transmission of reflections based upon the presence or absence of a activating condition; or the sensor may be positioned between the antenna and the microstrips; or the sensor may operate by changing at least one of the dielectric, electrical, mechanical, chemical, optical, or biological properties of the sensor in response to the activating condition; or the activating condition may be the presence of an organic gas.

Another chipless RFID tag system includes (a) a transmitter sending an input signal; (b) a tag substrate having at least one microstrip, the microstrip having a phase discontinuity altering the phase of a signal reflection at the discontinuity; and (c) a receiver detecting a change in phase between at least two reflections from the input signal and identifying relative time domain positions of the reflections based upon the phase change. This system may include the second transmission line being twice as long as the first line; or the transmission lines comprising microstrip lines; or the transmission lines being meandered; or one of the lines being substantially ground terminated and another of the lines being substantially open terminated; or the different lengths of transmission lines causing the signal reflections to have sufficient time period between the reflections to detect the phase change; or the different termination of the lines causing a detectable phase modulated pattern of at least two bits.

While many specific examples have been described above, it should be understood that the intention is not to limit the invention to the particular embodiments described. Rather, the intention is for the invention to encompass all modifications, equivalents, and alternatives falling within the spirit and scope of the following claims to the fullest extent allowable by law.

I claim:

1. A passive wireless sensor strip comprising:
   a substrate;
   a strip antenna positioned on the substrate, and the strip antenna having an alterable reflection characteristic; and
   a passive sensor device positioned on the substrate and connected to the strip antenna, and the passive sensor device altering the reflection characteristics of the strip antenna when exposed to ethylene gas;
   wherein the sensor device comprises a layer of semi-conductor material positioned between two conducting layers; and
   wherein at least one of the conducting layers comprises an antenna lead connecting the strip antenna to the passive sensor device.

2. A passive wireless sensor strip comprising:
   a substrate;
   a strip antenna positioned on the substrate, and the strip antenna having an alterable reflection characteristic; and
   a passive sensor device positioned on the substrate and connected to the strip antenna, and the passive sensor device altering the reflection characteristics of the strip antenna when exposed to a target condition;
   wherein the sensor device changes capacitance upon exposure to ethylene gas, the target condition being whether the strip antenna is exposed to the ethylene gas.

3. The passive wireless sensor strip of claim 1, wherein the layer of semi conductor material comprises tin dioxide.

4. The passive wireless sensor strip of claim 1, wherein the target condition is ethylene gas.

5. The passive wireless sensor strip of claim 1, wherein the substrate is flexible.

6. The passive wireless sensor strip of claim 2, wherein the sensor device comprises a layer of semi conductor material positioned between two conducting layers.

7. The passive wireless sensor strip of claim 2, further comprising an antenna lead connecting the strip antenna to the passive sensor device, and one of the conducting layers comprises the antenna lead.

8. The passive wireless sensor strip of claim 3, wherein the tin dioxide is doped.

9. The passive wireless sensor strip of claim 1, wherein the sensor device changes capacitance upon exposure to a target gas, the target condition being whether the strip antenna is exposed to the target gas.

10. The passive wireless sensor strip of claim 1, wherein the sensor device changes capacitance upon exposure to the ethylene gas.

* * * * *